US007970624B2

(12) United States Patent
Anderson et al.

(10) Patent No.: US 7,970,624 B2
(45) Date of Patent: Jun. 28, 2011

(54) SYSTEM AND USER INTERFACE FOR PRESENTING TREATMENT INFORMATION

(75) Inventors: Jean Anderson, Phoenixville, PA (US); Loretta A. Fitzgerald, Collegeville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1636 days.

(21) Appl. No.: 11/120,764

(22) Filed: May 3, 2005

(65) Prior Publication Data

US 2006/0085223 A1 Apr. 20, 2006

Related U.S. Application Data

(60) Provisional application No. 60/616,519, filed on Oct. 6, 2004.

(51) Int. Cl.
*G06Q 10/00* (2006.01)
*G06F 19/00* (2006.01)

(52) U.S. Cl. ............................... 705/2; 705/3
(58) Field of Classification Search .......... 705/2–3; 600/436; 378/65; 235/380
See application file for complete search history.

(56) References Cited

U.S. PATENT DOCUMENTS

| 6,142,925 | A  | * | 11/2000 | Siochi et al. ............. 600/1 |
| 6,464,136 | B2 |   | 10/2002 | Walsh |
| 6,497,358 | B1 | * | 12/2002 | Walsh ..................... 235/380 |
| 6,650,930 | B2 | * | 11/2003 | Ding ....................... 600/436 |
| 6,792,073 | B2 | * | 9/2004  | Deasy et al. ............ 378/65 |
| 6,824,052 | B2 |   | 11/2004 | Walsh |
| 2002/0046062 | A1 |  | 4/2002 | Kameda |
| 2003/0050801 | A1 |  | 3/2003 | Ries et al. |
| 2003/0065537 | A1 |  | 4/2003 | Evans |
| 2004/0016799 | A1 |  | 1/2004 | Walsh |
| 2004/0021693 | A1 |  | 2/2004 | Monteleone |
| 2005/0055242 | A1 | * | 3/2005 | Bello et al. ............. 705/2 |

OTHER PUBLICATIONS

NCI Tools, University of North Carolina at Chapel Hill, http://www.radonc.unc.edu/tools/home.html.
Quick Summary for Programmers http://www.radonc.unc.edu/tools/summary.
NCI Tools Reports, papers & specifications http://www.radonc.unc.edu/tools/reports.html.
What is the NCI Tools Project? http://www.radonc.unc.edu/tools/whatis.html.
NCI Tools Minimum Requirements http://www.radonc.unc.edu/tools/minquals.html.
New Image-Guided Radiotherapy Treatment Planning Software from Varian http://www.appliedradiolocry.com/options/printer.asp?. International Search Report.

* cited by examiner

*Primary Examiner* — Luke Gilligan
*Assistant Examiner* — Joseph Burgess
(74) *Attorney, Agent, or Firm* — Alexander J Burke

(57) ABSTRACT

A workflow system and user interface coordinates information concerning a course of treatment of a patient, as well as data from a treatment device and links appointment data from a scheduling system with actual treatment activity information in order to show a complete timeline of a course of treatment. A user interface system for presenting medication dosage and treatment information includes a display processor for providing data representing a single display image. The single display image presents information identifying treatment received by a patient and treatment scheduled to be received by the patient together with a timeline. The single display image also presents information identifying cumulative dosage of a medication received by a patient and an associated date the cumulative dosage is received by the patient. A command processor initiates presentation of the single display image in response to user command.

23 Claims, 4 Drawing Sheets

US 7,970,624 B2

SYSTEM AND USER INTERFACE FOR PRESENTING TREATMENT INFORMATION

This is a non-provisional application of provisional application Ser. No. 60/616,519 by J. Anderson et al. filed Oct. 6, 2004.

FIELD OF THE INVENTION

This invention concerns a system for integrating clinical information, treatment planning and scheduling systems and providing a user interface presenting medication dosage and treatment information.

BACKGROUND OF THE INVENTION

In existing medical information systems including Radiation Oncology information systems, for example, clinicians track a treatment course of action and results using manual tools and spreadsheets that typically fail to provide a forward view of a treatment plan. Existing systems are usually limited to showing the history of treatment administration in text format or graphical display. Existing systems also fail to correlate planned treatment to actual treatment across a time period in a graphic format with drill down capabilities. In such systems clinicians (e.g., Oncologists) need to switch between two or more information sources, manual or electronic, to develop a composite view of planned treatment and actual treatment as well as treatment tolerance. This is burdensome, requiring additional resources, time and supplementary verification of information. A system according to invention principles addresses these deficiencies and related problems.

SUMMARY OF INVENTION

The inventors have recognized the advantages of displaying both planned and actual treatment and results in the same composite User Interface (UI) display image. A workflow system and user interface facilitates providing a clinician with an overall view of a treatment schedule in both the present and future and enables a clinician to view a patient treatment plan and determine how far along in the treatment a patient is and to gauge patient reaction to a treatment. A user interface system for presenting medication dosage and treatment information includes a display processor for providing data representing a single display image. The single display image presents information identifying treatment received by a patient and treatment scheduled to be received by the patient together with a timeline. The single display image also presents information identifying cumulative dosage of a medication received by a patient and an associated date the cumulative dosage is received by the patient. A command processor initiates presentation of the single display image in response to user command.

DETAILED DESCRIPTION OF THE INVENTION

Figure 1:
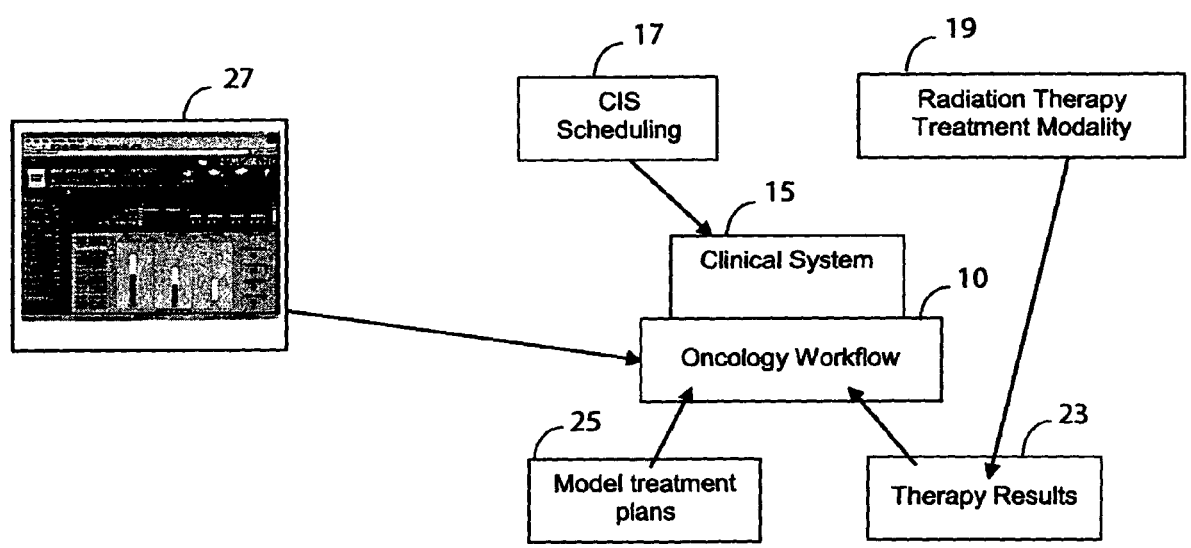
FIG. 1 shows a system for integrating clinical, treatment planning and scheduling information and providing a user interface presenting medication dosage and treatment information, according to invention principles.

A workflow and user interface (UI) system provides clinicians with an overall view of a treatment schedule covering both the present and future time periods and also provides easy access to detailed treatment information. The workflow and user interface system enables a clinician to see a patient treatment plan and determine how far along in treatment a patient is, and how much of the treatment plan remains to be performed. The workflow and user interface system manages patient care in a radiation oncology department by providing a streamlined user interface embedded into a workflow of an oncologist, for example. It allows a clinician to see an overall timeline or calendar overview of a patient's treatment. It shows temporal relationships of treatment related data segments and facilitates user navigation into detailed information concerning a particular treatment segment. The workflow and user interface system coordinates detailed information concerning a course of treatment of a particular patient with data from a treatment device and also links appointment data from a scheduling system with information concerning actual treatment activities in order to provide a complete timeline of a course of treatment of a patient. Radiation oncologists are advantageously able to use a single workflow to evaluate treatment and adjust parameters. A clinician uses the system to assess seriousness (severity) of a patient reaction to a particular treatment (e.g., radiation or chemotherapy treatment). An oncologist using the system may alter treatment dosage or duration upon determination that a patient experiences adverse reactions in an early stage of therapy. The stage at which treatment is being administered in a treatment plan is significant because, for example, later in the treatment cycle, the same adverse reactions may not require a change of dosage or duration.

An executable application as used herein comprises code or machine readable instruction for implementing predetermined functions including those of an operating system, healthcare information system or other information processing system, for example, in response user command or input. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device. Further, workflow comprises a task sequence for performance by one or a combination of, a healthcare worker, device or software.

FIG. 1 shows a system for integrating clinical, treatment planning and scheduling information and providing a user interface presenting medication dosage and treatment information. The system workflow aggregates and displays treatment information, including oncology radiation therapy information acquired from multiple systems to give a single composite user interface image. The composite user interface image provides navigational drill down capabilities supporting monitoring and changing of treatment plans based on patient current test results and observations. The system is integrated with a scheduling application for accessing date and time of scheduled (future) treatments and is integrated with a treatment delivery device to access information concerning previously administered treatments.

The FIG. 1 system and user interface provides clinical information, derived via interfaces with oncology diagnosis and treatment equipment, to a Clinical Information System, for example. The user interface provides a composite graphical view of treatment plan and actual results as well as navigation capabilities facilitating determination of factors that are adjustable to improve both tolerance of a therapy and a positive treatment outcome. Workflow engine 10 is an oncology workflow management unit in this example but may manage workflow associated with other medical conditions in other embodiments. Workflow engine 10 advantageously generates a display image providing a comprehensive overview of detailed patient treatment related information and user friendly navigation capabilities and access to the patient treatment related information. Workflow engine 10 acquires and processes a variety of data objects from multiple different executable applications. Specifically, workflow engine 10 accesses data objects from, an appointment management application and scheduling application 17, treatment plan information from a treatment planning system 25, treatment event information from a treatment device (e.g., radiation therapy unit 19) as well as therapy and results information from unit 23. Workflow engine 10 also accesses patient medical record information and diagnosis information from clinical information system 15. The information items acquired by workflow engine 10 for a particular patient are mutually associated by unit 10 and stored in at least one repository in unit 10.

Figure 2:
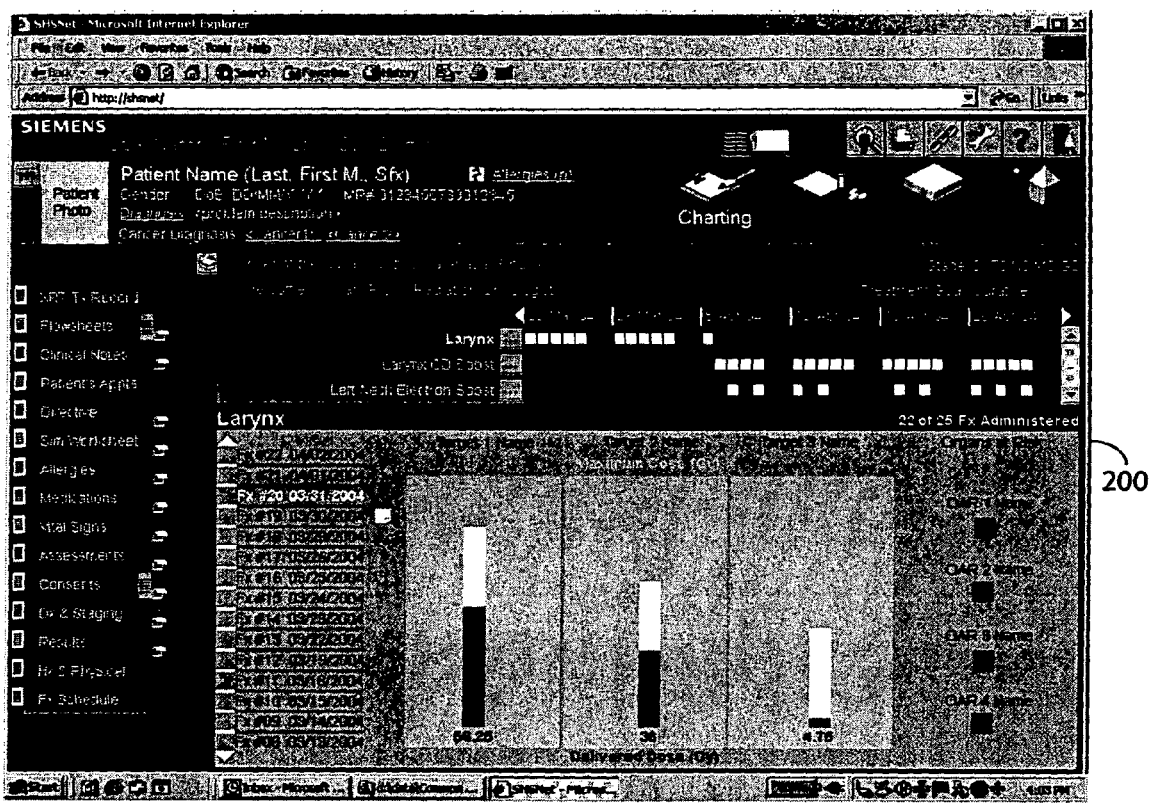
FIG. 2 shows a single User Interface (UI) composite display image presenting both planned and actual treatment and results data, according to invention principles.

The information items stored in a repository in unit 10 are processed by unit 10 to create display images for presentation on user interface device 27. FIG. 2 shows a single User Interface (UI) composite display image presenting both planned and actual treatment and results data provided by workflow engine 10. The composite display image 200 advantageously associates a course of treatment calendar that shows an overall treatment plan together with a treatment delivery timeline that shows a treatment administration history. The composite display image supports user friendly access (e.g. via single mouse-click selection) to information concerning the history of treatment (e.g., a radiation therapy treatment record) of a particular patient or the future treatment of a particular patient.

Figure 3:
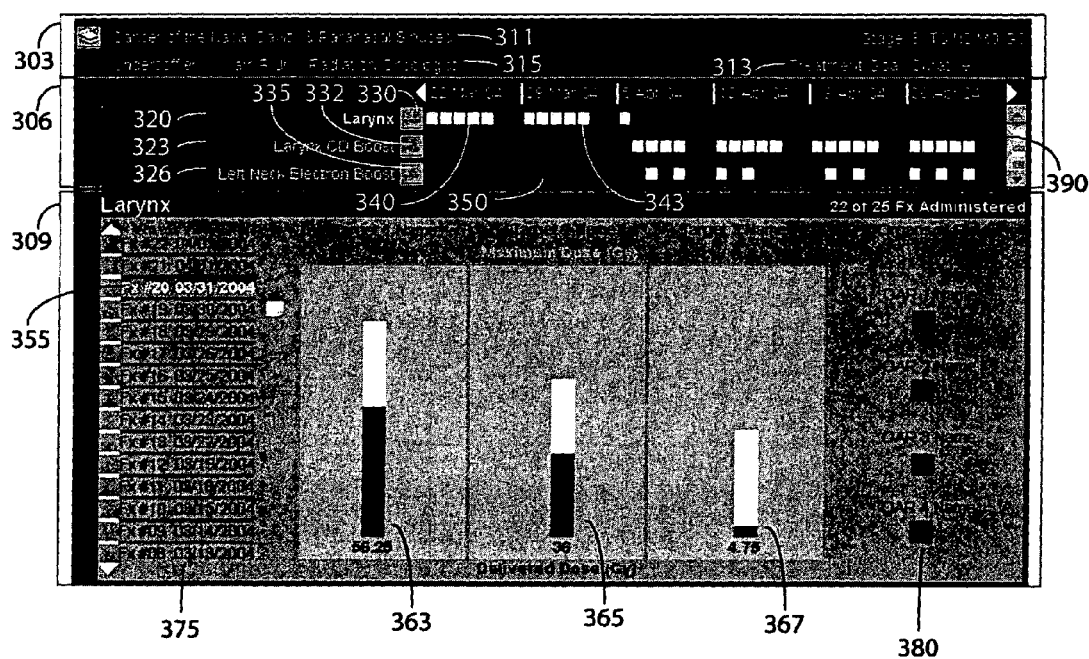
FIG. 3 shows a portion of the single User Interface (UI) composite display image of FIG. 2, according to invention principles.

FIG. 3 shows a portion of the single User Interface (UI) composite display image of FIG. 2. Image area 303 includes data concerning a course of treatment of a particular patient. Area 303 includes data items identifying, a diagnosis 311 of the particular patient that is being treated, a goal 313 of the treatment and a physician 315 that is in charge of the treatment. Image area 306 includes data concerning phases of treatment and their schedules. An individual phase of treatment has its own row. Three rows are visible at a time, Larynx 320, Larynx CD Boost 323, Left Neck Electron Boost 326, in this example. In another embodiment a different number of rows may be present. User selectable buttons 330, 332 and 335 on each row launch a smaller image window with details of treatment prescribed for the corresponding treatment phase. A row, e.g., row 320, (and corresponding treatment phase) that is currently selected is indicated by a display attribute such as color (or in other embodiments, highlighting, shading, symbol, text or other characteristic). White boxes (e.g., boxes 340, 343) in calendar 390 indicate that treatment for a particular phase is delivered or to be delivered on that date. The current day (and in another embodiment a current portion of the day such as a time period of the day) 350 is also indicated by a display attribute such as color of a particular calendar column. In other embodiments, the current day (and current portion of the day) may be indicated by a display image attribute such as highlighting, shading, symbol, text or other characteristic. Calendar 390 presents six weeks of treatment information. However, a clinician is able to scroll forward to the end of the course of treatment or back to the beginning of the course of treatment. In another embodiment, a period of time that is greater or less than six weeks may be presented in calendar 390.

Image area 309 presents information indicating treatment delivered or to be delivered for a currently selected corresponding phase of treatment indicated in a currently selected row of rows 320, 323, and 326, selected in response to user activation of a corresponding button 330, 332 and 335. Treatment administration events are shown in image area 309 in a reverse chronological timeline 375 along the left side of image area 309. A selected treatment administration event 355 is indicated by white boldface text. Image area 309 includes one or more bar charts such as bar charts 363, 365 and 367. Bar charts 363, 365 and 367 individually compare a cumulative treatment dose administered to three corresponding different target anatomical sites with a total dose prescribed to be administered to the three target anatomical sites. In this embodiment, image area 309 includes a maximum of three bar charts but in another embodiment may be limited to a different number of bar charts. The treatment doses indicated in bar charts 363, 365 and 367 comprise medication or therapy (such as radiation therapy) doses administered to corresponding particular target anatomical sites of a particular patient.

A user is able to select any treatment administration event in timeline 375 to initiate display of a bar chart indicating a cumulative dose administered to a particular target anatomical site of a particular patient at a time associated with a user selected treatment administration event. A user is also able to select a bar chart associated with a particular target anatomical site of a particular patient to view information concerning a treatment dose administered to that particular target anatomical site. Data items indicating treatment events in timeline 375 are individually associated with a corresponding user selectable button or link (e.g., a hyperlink). A treatment event associated button or link is selectable by a user to initiate launch of an image window including information comprising a record of treatment administered to a target anatomical site of a particular patient in the treatment event by a treatment device (e.g., a radiation therapy device). Column 380 of image 309 also provides status indicators indicating whether other critical structures of the particular patient are endangered or not. Other critical structures of a particular patient may be endangered if they cannot be fully shielded from therapeutic radiation or may be endangered by side effects of a medication such as chemotherapy, for example.

The FIG. 3 user interface image portion advantageously combines a calendar overview of a course of treatment with a timeline of treatment administration information. Workflow engine 10 (FIG. 1) integrates treatment calendar, treatment plan, scheduling and results information. Workflow engine 10 provides alert messages to a clinician that are triggered by acquired patient parameters or treatment device parameters that are outside of predetermined tolerance limit values. The alert messages enable an oncology clinician, for example to more quickly identify subtle changes in treatment, outcome and patient clinical status enabling the clinician to adjust a treatment process to the needs of a particular patient.

Workflow engine 10 acquires, coordinates and processes information concerning a course of treatment of a patient and stores data from a treatment device in a patient medical record. Workflow engine 10 also links patient appointment information acquired from a scheduling system with actual treatment activity information in order to show a complete timeline of occurrences in a course of treatment. The system is applicable to other medical and oncology treatments such as medical oncology to evaluate chemotherapy treatment and is applicable to other therapies that are administered over an extended period of time and that involve recording data for comparison with measurable objectives. Such treatments include, physical therapy to improve range of limb movement for a post-surgical patient, for example.

Figure 4:
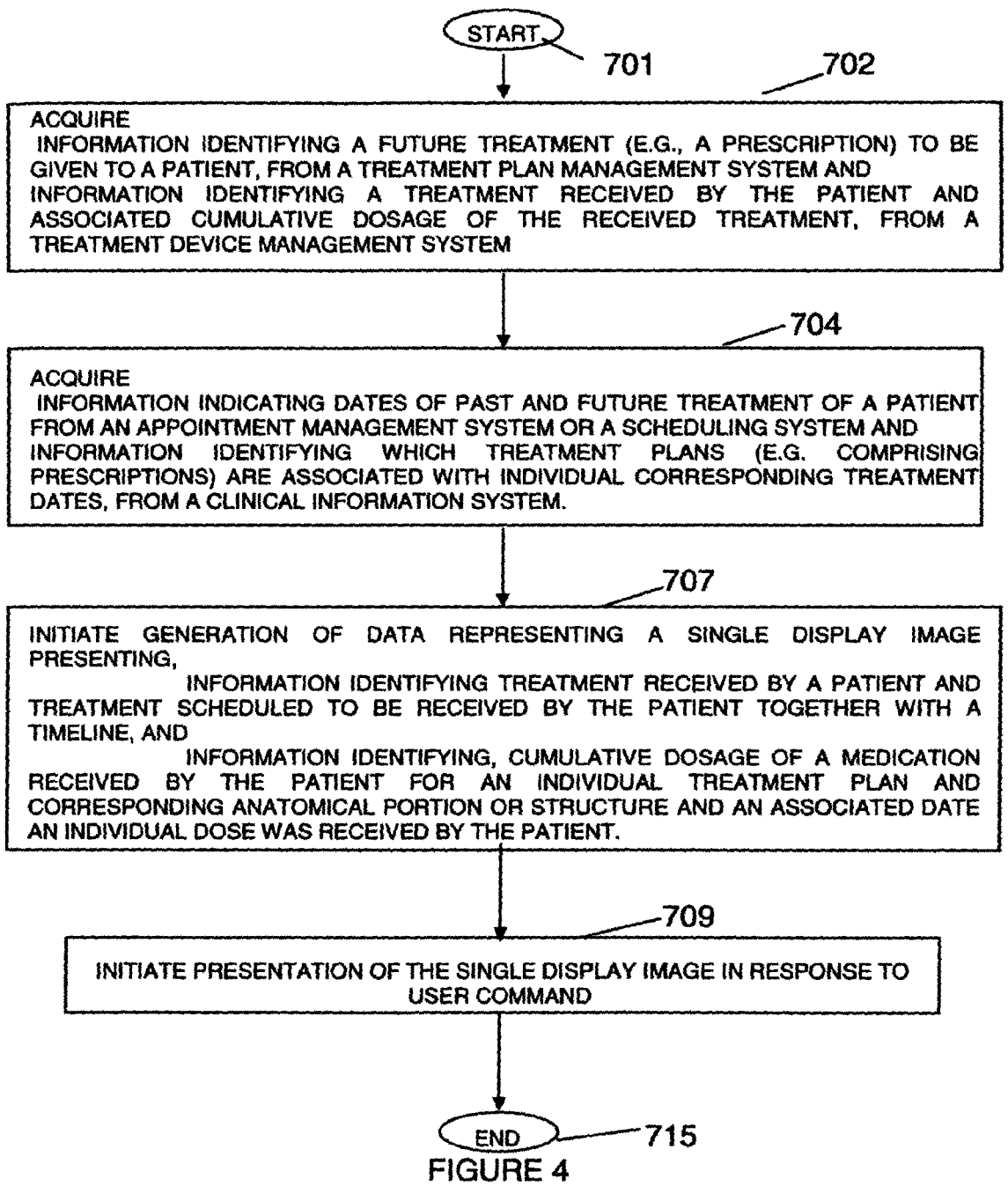
FIG. 4 shows a flowchart of a process for providing a single User Interface (UI) composite display image, according to invention principles.

FIG. 4 shows a flowchart of a process for providing a single User Interface (UI) composite display image. In activity 702 following the start at activity 701, workflow engine 10 acquires information identifying treatment to be provided to a patient from a treatment plan management system and information identifying a received treatment and associated cumulative dose of the received treatment, from a treatment device management system. Workflow engine 10 in activity 704, acquires information indicating dates of future treatment and past treatment from at least one of, (a) an appointment management system and (b) a scheduling system and also acquires information identifying a treatment plan associated with a corresponding treatment date, from a clinical information system. The information identifying treatment to be provided to a patient comprises a prescription, for example. The medication comprises a drug, an infusion or a therapeutic agent such as radiation therapy, for example.

A cumulative dose of a therapeutic agent, such as a cumulative radiation dosage, is of clinical significance in patient treatment. The radiation may be provided by a radiation source internal to a patient or by a source external to the patient. A radiation source internal to a patient may comprise an implanted device, an intra-vascular radiation treatment source, a temporarily inserted radiation source, a permanently inserted radiation source, a diagnostic related radiation source or a therapeutic radiation source.

In activity 707, workflow engine 10 initiates generation of data representing a single display image. The single display image presents information identifying treatment received by a patient and treatment scheduled to be received by the patient together with a timeline. The timeline indicates at least one of, (a) a date, (b) a date range and (c) a time, the treatment was received or was scheduled to be received, by the patient. The treatment scheduled to be received by the patient comprises multiple different treatments and the single display image presents information identifying multiple different treatments as being scheduled to be received concurrently or sequentially. The treatment comprises a drug, active therapy, imaging, tests or surgery. Active therapy comprises at least one of, (i) radiation therapy, (ii) chemotherapy, (iii) anesthesiology, (iv) laser therapy, (v) light therapy and (vi) other anatomically altering therapy, for example. The single display image also presents multiple individually user selectable data items representing corresponding multiple different phases of patient treatment. The single display image indicates at least one of, (a) a currently selected phase of patient treatment and (b) a currently selected date in the timeline using a display attribute comprising at least one of, (i) highlighting, (ii) color, (iii) text, (iv) a symbol, (v) shading and (vi) shape.

The single display image also presents information identifying cumulative dosage of a medication received by the patient for an individual treatment plan and corresponding anatomical structure or portion as well as an associated date the individual dose was received by the patient. The single display image presents the information identifying cumulative dosage of the medication together with information identifying a total dosage to be scheduled to be received by the patient in a course of treatment. The single display image indicates the cumulative dosage of the medication as a proportion of the total dosage. The information identifying cumulative dosage of the medication received by the patient is presented together with a timeline. The timeline indicates at least one of, a date, a date range and a time, a cumulative dosage of the medication was received by the patient. Workflow engine 10 in activity 709 initiates presentation of the single display image to a user on a reproduction device such as on user interface device 27 (FIG. 1) in response to user command. The process of FIG. 4 terminates at activity 715.

The system, processes and user interface menus presented in FIGS. 1-4 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided by the systems of FIG. 1 and process of FIG. 4 may be implemented in hardware, software or a combination of both.

What is claimed is:

1. A user interface system for processing medication dosage and treatment information, comprising:
at least one processing device including,
a display processor for providing data representing a single display image presenting,
information identifying a particular phase of a course of radiation treatment comprising a plurality of different concurrent phases of radiation treatment received by a patient and radiation treatment scheduled to be received by said patient together with a calendar presenting a time period of at least a week indicating when said particular phase of radiation treatment is scheduled to be received and radiation treatments associated with said particular phase of radiation treatment previously received by said patient, and
information identifying cumulative dosage of a medication received by a patient during a plurality of radiation treatments administered on a plurality of different occasions and associated dates said cumulative dosage is received by said patient, wherein said medication is radiation and said cumulative medication dosage is a cumulative radiation dosage;
a command processor for initiating presentation of said single display image in response to user command; and
a workflow engine, coupled to said command processor and said display processor, for providing alert messages to a user in response to at least one of, (a) an acquired patient parameter and (b) a treatment device parameter including a cumulative dosage exceeding a predetermined tolerance limit value.

2. A system according to claim 1, wherein said workflow engine provides an alert message, to a clinician via a display image, that is triggered by treatment device parameters that are outside of predetermined tolerance limit values, said alert message identifying change in treatment and patient clinical status and prompting the clinician to adjust a treatment process to the needs of a particular patient and
    said single display image presents information identifying cumulative dosage of said medication received by a patient for an individual treatment plan and corresponding anatomical structure or portion as well as an associated date said individual dose was received by said patient.

3. A system according to claim 2, wherein
    said information identifying treatment scheduled to be received by said patient comprises a prescription.

4. A system according to claim 1, wherein said radiation is provided by a radiation source internal to said patient and comprises at least one of, (a) an implanted device, (b) an intra-vascular radiation treatment source, (d) a temporarily inserted radiation source, (e) a permanently inserted radiation source, (f) a diagnostic related radiation source and (g) a therapeutic radiation source.

5. A system according to claim 1, wherein
    said radiation is from one or more sources external to said patient.

6. A system according to claim 1, wherein said information identifying cumulative dosage of said medication received by a patient is presented together with a calendar and identifies cumulative dosage at a plurality of different anatomical locations.

7. A system according to claim 6, wherein said calendar indicates at least one of, (a) a date, (b) a date range and (c) a time, said cumulative dosage of said medication was received by said patient.

8. A system according to claim 1, wherein said single display image presents information identifying a plurality of different phases of treatment concurrently received by a patient over a course of treatment enabling a user to select a particular phase of treatment from said plurality of different phases and
    said calendar indicates at least one of, (a) a date, (b) a date range and (c) a time, said treatment was received by said patient.

9. A system according to claim 8, wherein said single display image presents information identifying a plurality of different treatment administration events together with a timeline comprising a time period of at least a week for a selected particular phase of radiation treatment and said calendar indicates at least one of, (a) a date, (b) a date range and (c) a time, said treatment is scheduled to be received by said patient.

10. A system according to claim 1, wherein
    said medication comprises at least one of, (a) a drug and (b) an infusion.

11. A system according to claim 1, wherein said medication received by said patient during said plurality of treatments administered on said plurality of different occasions has accumulative effects and a cumulative dose is of clinical significance in patient treatment.

12. A system according to claim 1, wherein
    said treatment scheduled to be received by said patient comprises a plurality of different treatments and said single display image presents information identifying said plurality of different treatments as being scheduled to be received at least one of, (a) concurrently and (b) sequentially.

13. A system according to claim 1, wherein
    said treatment comprises at least one of, (a) a drug, (b) active therapy, (e) imaging, (d) tests and (e) surgery.

14. A system according to claim 13, wherein said active therapy comprises at least one of, (i) radiation therapy, (ii) chemotherapy, (iii) anesthesiology, (iv) laser therapy, (v) light therapy and (vi) other anatomically altering therapy.

15. A system according to claim 1, wherein said single display image presents said information identifying cumulative dosage of said medication together with information identifying a total dosage to be scheduled to be received by said patient in a course of treatment.

16. A system according to claim 15, wherein
    said single display image indicates said cumulative dosage of said medication as a proportion & said total dosage.

17. A system according to claim 1, wherein said single display image presents a plurality of individually user selectable data items representing a plurality of corresponding different phases of patient treatment.

18. A system according to claim 17, wherein said single display image indicates at least one of, (a) a currently selected phase of patient treatment and (b) a currently selected date in said calendar using a display attribute comprising at least one of, (i) highlighting, (ii) color, (iii) text, (iv) a symbol, (v) shading and (vi) shape.

19. A user interface system for processing medication dosage and treatment information, comprising:
    at least one processing device including,
    an acquisition processor for acquiring information identifying a particular phase of a course of radiation treatment comprising a plurality of different concurrent phases of radiation treatment to be provided to a patient from a treatment plan management system and information identifying a received radiation treatment and associated cumulative dose of the received radiation treatment from a treatment device management system;
    a display processor for providing data representing a single display image presenting,
    said information identifying said received radiation treatment and radiation treatment to be provided to said patient together with a calendar presenting a time period of at least a week derived using said information indicating dates of future radiation treatment and indicating when said radiation treatment is scheduled to be received and treatments associated with said particular phase of radiation treatment previously received by said patient, and
    information identifying cumulative dosage of a medication received by a patient during a plurality of radiation treatments administered on a plurality of different occasions and associated dates said cumulative dosage is received by said patient, wherein said medication is radiation and said cumulative medication dosage is a cumulative radiation dosage; and
    a command processor for initiating presentation of said single display image in response to user command; and
    a workflow engine, coupled to said command processor and said display processor, for providing alert messages to a user in response to at least one of, (a) an acquired patient parameter and (b) a treatment device parameter including a cumulative dosage exceeding a predetermined tolerance limit value.

20. A system according to claim 19, wherein said acquisition processor acquires information indicating dates of future treatment and past treatment from at least one of, (a) an appointment management system and (b) a scheduling system.

21. A system according to claim 20, wherein said information identifying treatment to be provided to said patient comprises a prescription.

22. A system according to claim 19, further comprising an acquisition processor for acquiring information identifying a treatment plan associated with a corresponding treatment date, from a clinical information system.

23. A method for providing a user interface for processing medication dosage and treatment information, comprising the activities of:

employing at least one processing device for, initiating generation of data representing a single display image presenting, information identifying a particular phase of a course of radiation treatment comprising a plurality of different concurrent phases of radiation treatment received by a patient and radiation treatment scheduled to be received by said patient together with a calendar presenting a time period of at least a week indicating when said particular phase of radiation treatment is scheduled to be received and radiation treatments associated with said particular phase of radiation treatment previously received by said patient, and information identifying cumulative dosage of a medication received by a patient during a plurality of radiation treatments administered on a plurality of different occasions and on associated dates said cumulative dosage is received by said patient, wherein said medication is radiation and said cumulative medication dosage is a cumulative radiation dosage;

initiating presentation of said single display image in response to user command; and generating alert messages to a user in response to at least one of, (a) an acquired patient parameter and (b) a treatment device parameter including a cumulative dosage exceeding a predetermined tolerance limit value.

* * * * *